US010849526B1

(12) United States Patent
Demir et al.

(10) Patent No.: US 10,849,526 B1
(45) Date of Patent: Dec. 1, 2020

(54) SYSTEM AND METHOD FOR BIO-INSPIRED FILTER BANKS FOR A BRAIN-COMPUTER INTERFACE

(71) Applicants: Ali Fatih Demir, Tampa, FL (US); Ismail Uysal, Lakeland, FL (US); Huseyin Arslan, Tampa, FL (US)

(72) Inventors: Ali Fatih Demir, Tampa, FL (US); Ismail Uysal, Lakeland, FL (US); Huseyin Arslan, Tampa, FL (US)

(73) Assignee: University of South Florida, Tampa, FL (US)

( * ) Notice: Subject to any disclaimer, the term of this patent is extended or adjusted under 35 U.S.C. 154(b) by 561 days.

(21) Appl. No.: 15/783,643

(22) Filed: Oct. 13, 2017

Related U.S. Application Data

(60) Provisional application No. 62/407,828, filed on Oct. 13, 2016.

(51) Int. Cl.
*A61B 5/0484* (2006.01)
*A61B 5/04* (2006.01)
*A61B 5/00* (2006.01)

(52) U.S. Cl.
CPC ...... *A61B 5/04842* (2013.01); *A61B 5/04017* (2013.01); *A61B 5/7203* (2013.01); *A61B 5/7264* (2013.01)

(58) Field of Classification Search
CPC ............ A61B 5/04842; A61B 5/04017; A61B 5/7203; A61B 5/7264
USPC .................................................. 600/544-545
See application file for complete search history.

(56) References Cited

U.S. PATENT DOCUMENTS

| | | | | |
|---|---|---|---|---|
| 6,602,202 | B2* | 8/2003 | John | A61B 5/04845 600/544 |
| 7,014,613 | B2* | 3/2006 | John | A61B 5/04845 600/559 |
| 7,399,282 | B2* | 7/2008 | John | A61B 5/04845 600/559 |
| 9,357,941 | B2* | 6/2016 | Simon | A61B 5/0476 |
| 2001/0049480 | A1* | 12/2001 | John | A61B 5/121 600/559 |

(Continued)

OTHER PUBLICATIONS

Demir et al., Bio-inspired Filter Banks for SSVEP-based Brain-computer Interfaces. IEEE International Conference on Biomedical and Health Informatics (BHI). Las Vegas, NV, USA. Feb. 24-27, 2016: 1-4.

(Continued)

*Primary Examiner* — Navin Natnithithadha
(74) *Attorney, Agent, or Firm* — Molly L. Sauter; Smith & Hopen, P.A.

(57) ABSTRACT

A system and method of steady-state visual evoked potential (SSVEP) frequency detection using bio-inspired filter banks (BIFB) includes, acquiring electroencephalographic (EEG) signals from a subject in response to a repetitive visual stimulus, estimating the power spectral density (PSD) of the channel of the EEG signals including at least one SSVEP response, extracting one or more SSVEP response features from the estimated PSD of the channel using a bio-inspired filter bank (BIFB) and classifying the extracted SSVEP response features to determine if the detected SSVEP response frequency from the EEG signals acquired from the subject substantially matches the repetition frequency of the repetitive visual stimulus.

17 Claims, 4 Drawing Sheets

(56) References Cited

U.S. PATENT DOCUMENTS

| | | | | |
|---|---|---|---|---|
| 2004/0064066 A1* | 4/2004 | John | .................. | A61B 5/04845 |
| | | | | 600/559 |
| 2004/0204659 A1* | 10/2004 | John | .................. | A61B 5/04845 |
| | | | | 600/559 |
| 2009/0062676 A1* | 3/2009 | Kruglikov | ............ | A61B 5/0484 |
| | | | | 600/544 |
| 2012/0150545 A1* | 6/2012 | Simon | .................... | A61B 5/162 |
| | | | | 704/270 |
| 2012/0159656 A1* | 6/2012 | Gerber | .................. | A61B 5/048 |
| | | | | 800/3 |
| 2013/0130799 A1* | 5/2013 | Van Hulle | ................ | G06F 3/01 |
| | | | | 463/36 |
| 2013/0295016 A1* | 11/2013 | Gerber | ............... | A61B 5/04012 |
| | | | | 424/9.2 |
| 2015/0351655 A1* | 12/2015 | Coleman | .............. | A61B 5/0482 |
| | | | | 600/301 |
| 2016/0249841 A1* | 9/2016 | Gerber | ............... | A61B 5/04012 |
| | | | | 424/9.2 |

OTHER PUBLICATIONS

Bakardjian et al., Optimization of SSVEP brain responses with application to eight-command Brain—Computer Interface. Neuroscience letters. 2010. vol. 469: 34-38

Brunner et al. BNCI Horizon 2020: towards a roadmap for the BCI community. Brain-Computer Interfaces. 2015. vol. 2 (No. 1): 1-10.

Amiri et al., A review of P300, and hybrid P300/SSVEP brain-computer interface systems. Brain-Computer Interface Systems—Recent Progress and Future Prospects. 2013. Chapter 10: 1-21.

\* cited by examiner

SYSTEM AND METHOD FOR BIO-INSPIRED FILTER BANKS FOR A BRAIN-COMPUTER INTERFACE

CROSS-REFERENCE TO RELATED APPLICATIONS

This application claims priority to U.S. Provisional Patent Application No. 62/407,828, entitled "BIO-INSPIRED FILTER BANKS FOR SSVEP-BASED BRAIN-COMPUTER INTERFACES", having a filing date of Oct. 13, 2016, which is hereby incorporated by reference

FIELD OF INVENTION

The invention relates to brain-computer interfaces (BCIs). More specifically, the invention describes novel bio-inspired filter banks (BIFB) for a stead-state visual evoked potential (SSVEP) based brain-computer interface (BCI).

BACKGROUND OF THE INVENTION

Scientific advances in neuroscience and biomedical engineering enable a direct communication channel between the human brain and a computer. The electrical activity in the brain that is produced by neuronal postsynaptic membrane polarity changes can be monitored to detect the user's intentions. As illustrated in FIG. 1, a brain-computer interface (BCI) 100, 105, 110, 115 analyzes the brain signals and translate them into commands for external devices 120, such as a speller device, wheelchair, robotic arm or a drone, Since BCIs utilize the signals generated by the central nervous system, the primary target of this technology is people with severe neuromuscular disorders (e.g., amyotrophic lateral sclerosis, brainstem stroke, spinal cord injury, and cerebral palsy). However, advanced BCI systems serve healthy people as well by providing an alternate way of communication, control, and security. Hence, these systems have evolved to be a promising part of the body area network.

While there exist multiple approaches to measure the brain activity, electroencephalography (EEG) is widely used in BCI applications because of its high time resolution, which is essential for BCIs to work as real-time systems. EEG devices are also inexpensive and portable. Various EEG signals could serve to drive WIs. For example, a distinctive oscillation pattern in EEG is observed when a sensory stimulus, such as visual or auditory, is presented to a human. These oscillations are referred to as evoked potentials (EPs), and they disappear after a short period. If the stimulus is repeated at a regular rate, the EPs do not have time to decay, and it causes a periodic response which are referred to as steady-state evoked potentials. More specifically, a repetitive visual stimulus elicits steady-steady visual evoked potentials (SSVEPs) which are more prominent in the occipital region of the brain. The targets that evoke SSVEPs are encoded in various ways, and the users makes a selection by shifting their attention to the desired target in SSVEP based BCIs. Among other BCI modalities which depend on other EEG signals (e.g., slow cortical potentials, sensorimotor rhythms, and event-related potentials), SSVEP based BCIs have the advantage of a high information transfer rate (ITR) and a short training duration to learn to operate the device.

SSVEPs are sinusoidal-like waveforms, and they appear at the same fundamental frequency of the driving stimulus and its harmonics. Spontaneous oscillations (i.e., background activity), which are not related to the stimulation, exist in the EEG recordings as well and a good SSVEP detection algorithm is required to build a reliable SSVEP based BCI system. Numerous methods have been proposed for SSVEP recognition over the last decade. Power spectral density analysis (PSDA) is a typical approach used because, the distinctive features of SSVEPs are observed in the frequency domain. However, PSDA is susceptible to noise, and long durations are needed to increase the signal to noise ratio (SNR). A multivariable statistical method, namely canonical correlation analysis (CCA), is used to exploit the multiple channel covariance information to thereby enhance the SNR and provide a better detection accuracy compared to PSDA. Simple implementation, high robustness, and better ITR performance have made CCA attractive in SSVEP recognition research. On the other hand, CCA is not efficient at extracting the discriminative information embedded in the harmonic components of SSVEPs, and filter-bank canonical correlation analysis (FBCCA) has been proposed to handle this issue. Although FBCCA captures the distinct spectral properties of multiple harmonic frequencies successfully, it disregards the frequency selective nature of SSVEP response due to utilization filters with wide bandwidths. Furthermore, this approach neglects any correlation information between SSVEP responses at different frequencies.

Accordingly, what is needed in the art is an improved steady-state visual evoked potential (SSVEP) recognition system and method to be employed in brain-computer interfaces (BCIs).

SUMMARY OF INVENTION

In accordance with various embodiments, the present invention provides novel bio-inspired filter banks (BIFB) for a steady-state visual evoked potential (SSVEP) recognition system and associated method of use. The present invention introduces bio-inspired filter banks (BIFB) for a novel SSVEP recognition method. It is known that SSVEP response to a flickering visual stimulus is frequency selective and gets weaker as the frequency of the stimuli increases. In the proposed approach of the present invention, the gain and bandwidth of the filters are designed and tuned based on these characteristics while also incorporating harmonic SSVEP responses.

In a particular embodiment, a method for steady-state visual evoked potential (SSVEP) frequency detection using a bio-inspired filter bank (BIFB) is provided, including, acquiring electroencephalographic (EEG) signals from a subject in response to a repetitive visual stimulus, the repetitive visual stimulus having a known repetition frequency and the EEG signals comprising a channel including at least one steady-state visual evoked potential (SSVEP) response resulting from the repetitive visual stimulus. The method further includes, estimating the power spectral density (PSI)) of the channel of the EEG signals including the at least one SSVEP response and extracting one or more SSVEP response features from the estimated PSD of the channel using a bio-inspired filter bank (BIFB), the BIFB comprising a plurality of filters, wherein each of the plurality of filters of the bio-inspired filter bank (BIFB) comprises a gain and a bandwidth that is tuned based upon one or more biological characteristics of the subject. The method additionally includes classifying the extracted SSVEP response features to determine if the detected SSVEP response frequency from the EEG signals acquired from the subject substantially matches the repetition frequency of the repetitive visual stimulus.

In specific embodiment, the one or more biological characteristics of the subject include a subject-specific frequency sensitivity.

Additionally, the method may further include adjusting the gain and bandwidth of the bio-inspired filter bank (BIFB) over time to account for a time variance of the SSVEP response.

The present invention further includes, a system for steady-state visual evoked potential (SSVEP) frequency detection using a bio-inspired filter bank (BIFB) which comprises, a brain-computer interface comprising input circuitry for receiving EEG signals from a subject in response to a repetitive visual stimulus generated by the visual stimulus generator, the EEG signals comprising a channel including at least one steady-state visual evoked potential (SSVEP) response resulting from the repetitive visual stimulus. The system further includes one or more processors of the brain-computer interface for estimating the power spectral density (PSD) of the channel of the EEG signals including the at least one SSVEP response, for extracting one or more SSVEP response features from the estimated PSD of the channel using a bio-inspired filter bank (BIER), the BIFB comprising a plurality of filters, wherein each of the plurality of filters of the bio-inspired filter bank (BIFB) comprises a gain and a bandwidth that is tuned based upon one or more biological characteristics of the subject, and for classifying the extracted SSVEP response features to determine if the detected SSVEP response frequency from the EEG signals acquired from the subject substantially matches the repetition frequency of the repetitive visual stimulus.

In the system of the present invention, the one or more biological characteristics of the subject may include a subject-specific frequency sensitivity and the processor may further be configured to adjust the gain and bandwidth of the bio-inspired filter bank (BIFB) over time to account for a time variance of the SSVEP response.

In an exemplary embodiment, the bio-inspired filter bank (BIM) of the inventive system includes an array of band-pass filters having a center frequency at the known repetition frequency of the repetitive visual stimulus and the associated harmonics.

In another embodiment, the present invention includes, one or more non-transitory computer-readable media having computer-executable instructions for performing a method of running a software program on a computing device, the computing device operating under an operating system. A method is further included on the media for issuing instructions from the software program comprising, acquiring electroencephalographic (EEG) signals from a subject in response to a repetitive visual stimulus, the repetitive visual stimulus having a known repetition frequency and the EEG signals comprising a channel including at least one steady-state visual evoked potential (SSVEP) response resulting from the repetitive visual stimulus and estimating the power spectral density (PSD) of the channel of the EEG signals including the at least one SSVEP response. The method on the media further includes instructions for extracting one or more SSVEP response features from the estimated PSD of the channel using a bio-inspired filter bank (RIM), the BIFB comprising a plurality of filters, wherein each of the plurality of filters of the bio-inspired filter bank (BIFB) comprises a gain and a bandwidth that is tuned based upon one or more biological characteristics of the subject; and instructions for classifying the extracted SSVEP response features to determine if the detected SSVEP response frequency from the EEG signals acquired from the subject substantially matches the repetition frequency of the repetitive visual stimulus.

In one embodiment, the instructions on the media are directed to issuing instructions for one or more biological characteristics of the subject which include a subject-specific frequency sensitivity and for issuing instructions for adjusting the gain and bandwidth of the bio-inspired filter bank (BIFB) over time to account for a time variance of the SSVEP response.

Additionally, the method of the media includes issuing instructions from the software program for the bio-inspired filter bank (BIFB) which includes an array of band-pass filters having a center frequency at the known repetition frequency of the repetitive visual stimulus and the associated harmonics.

As such, in accordance with the present invention, an improved steady-state visual evoked potential (SSVEP) recognition system and method to be employed in brain-computer interfaces (BCIs) is provided incorporating a novel bio-inspired filter bank (BIFB).

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Brain-computer interfaces (BCI) have the potential to play a vital role in future healthcare technologies by providing an alternative way of communication and control. More specifically, steady-state visual evoked potential (SSVEP) based BCIs have the advantage of higher accuracy and higher information transfer rate (ITR). In order to fully exploit the capabilities of such devices, it is necessary to understand the features of SSVEPs and design a system considering its inherent characteristics.

In the present invention, bio-inspired filter banks (BIM) are introduced as a novel SSVEP frequency detection method. It is known that SSVEP response to a flickering visual stimulus is frequency selective and gets weaker as the frequency of the stimuli increases. In the proposed approach of the present invention, the gain and bandwidth of the filters are designed and tuned based on these characteristics. Furthermore, the proposed approach incorporates the variation of SSVEP response over time. This method not only improves the accuracy but also increases the number of available commands by allowing the use of stimuli frequencies that elicit weak SSVEP responses. The BIFB method of the present invention achieves reliable performance when tested on datasets available online and compared with well-known SSVEP frequency detection methods, namely power spectral density analysis (PSDA) and canonical correlation analysis (CCA). The results show the potential of a bio-inspired design which will be extended to include further SSVEP characteristics for future SSVEP based BCIs.

Figure 1:
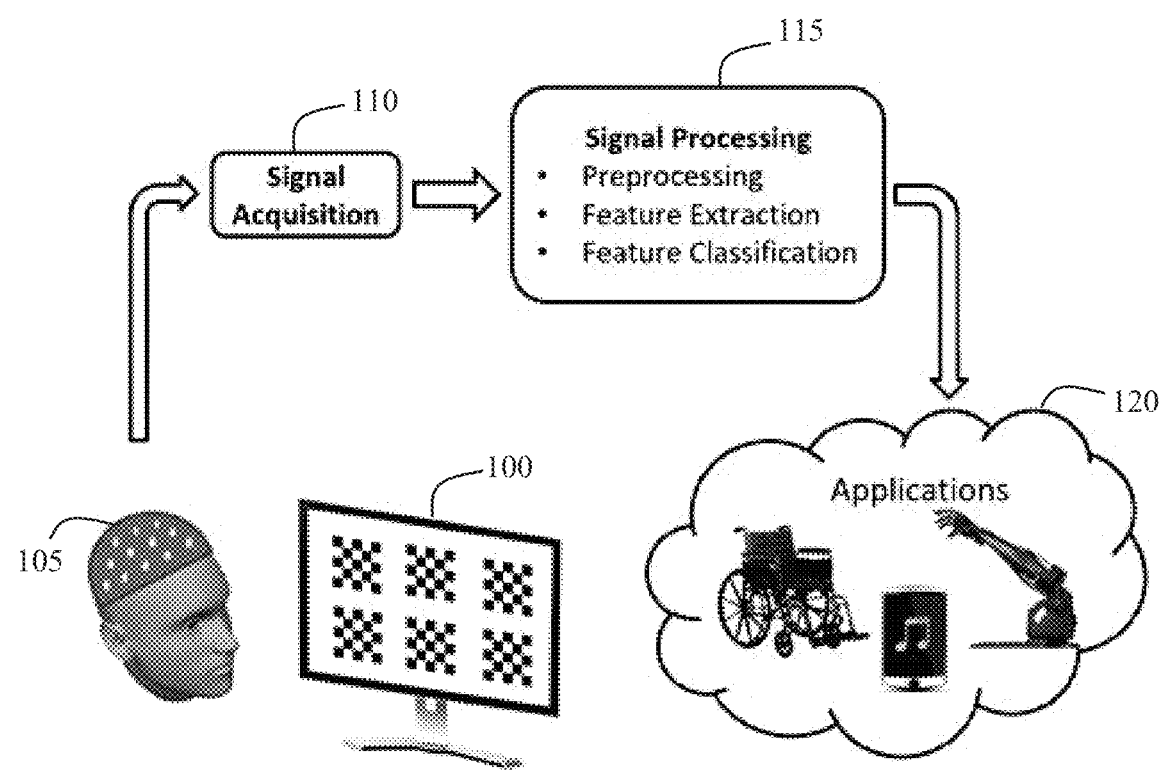
FIG. 1 is an image depicting a functional model of a steady-state visual evoked potential (SSVEP) brain-computer interface (BCI), in accordance with an embodiment of the present invention.
Figure 2:
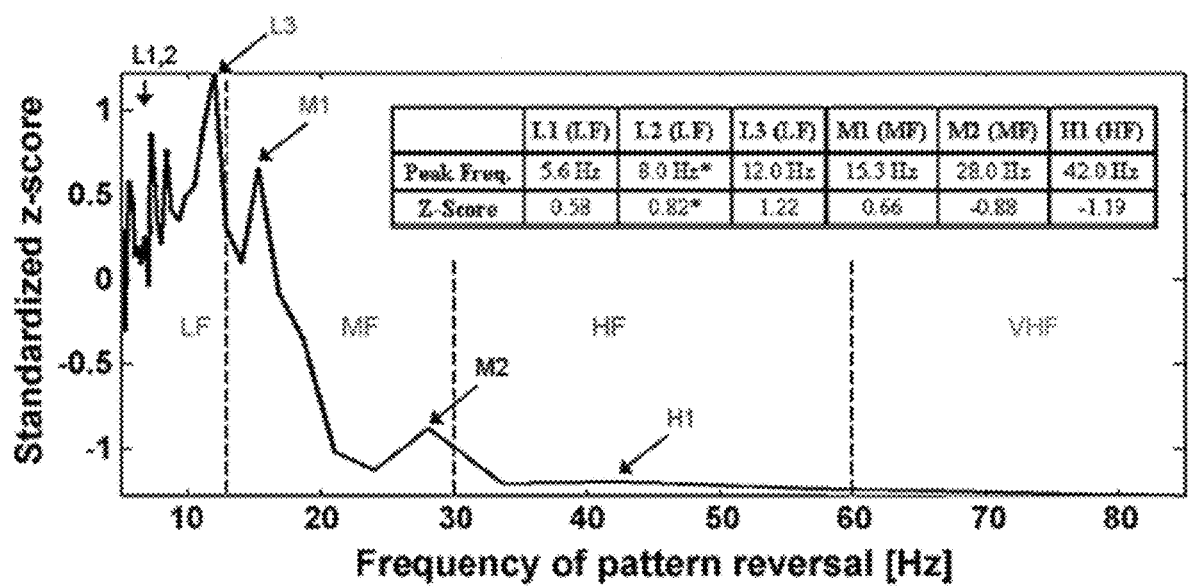
FIG. 2 is graphical illustration of the average brain frequency response to small-pattern reversal stimuli.
Figure 3:
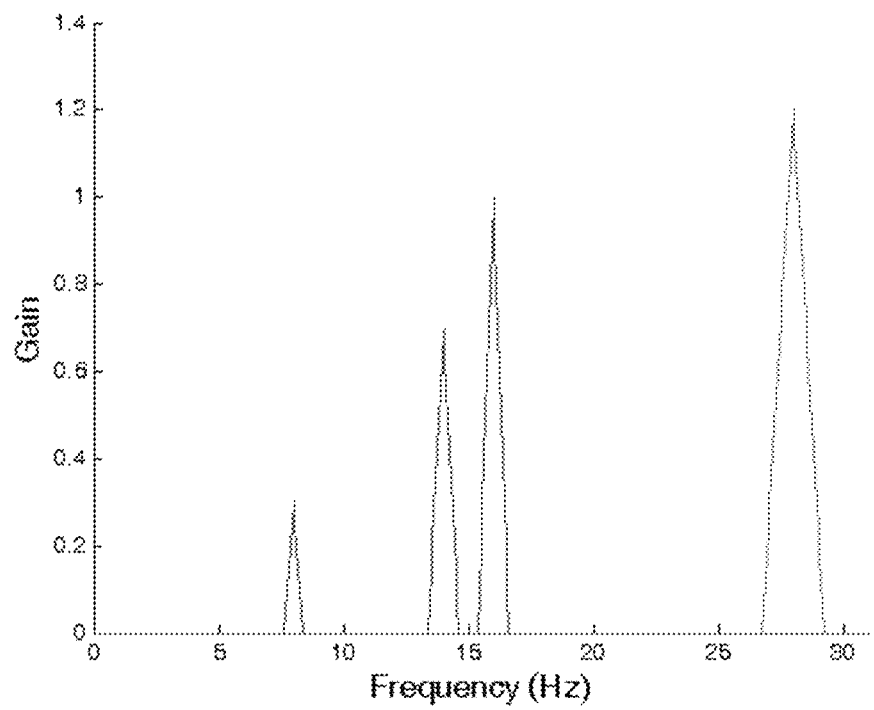
FIG. 3 is a graphical illustration of an exemplary bio-inspired filter bank (BLEB) design for a first dataset (A), in accordance with an embodiment of the present invention.
Figure 4:
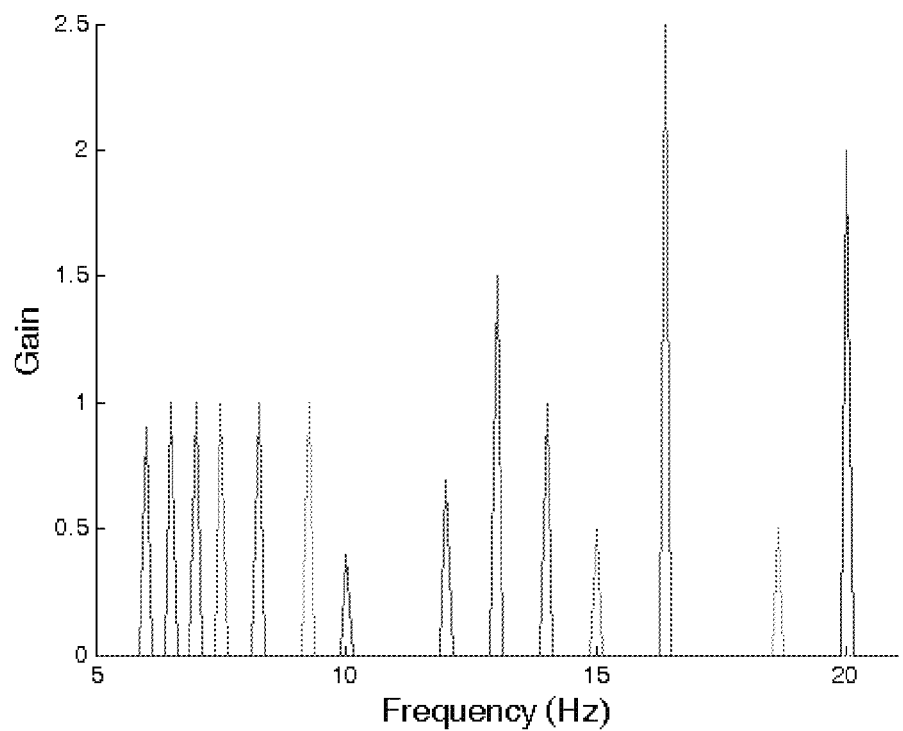
FIG. 4 is a graphical illustration of an exemplary bio-inspired filter bank (BIFB) design for a second dataset (B), in accordance with an embodiment of the present invention.

FIG. 2 illustrates the average SSVEP response over many subjects. The graph provides a general idea of how the SSVEP response power changes as the frequency of the stimulus changes. As such, as shown in FIG. 2, the SSVEP response power to a flickering visual stimulus is frequency selective and gets weaker as the frequency of the stimuli increases, Although the EEG background noise power decreases as well (approximately with a 1/f behavior), the resultant signal-to-noise (SNR) is still considerably low at higher frequencies. Accordingly, in the present invention, the gain and bandwidth of the bio-inspired filters are designed and tuned based on these characteristics while incorporating the variation of SSVEP response over time.

Two publicly-available datasets were utilized to test the results of the filter banks described by the present invention. Dataset-A, provided by one research institute, consisted of EEG recordings of four healthy subjects with normal or corrected to normal vision. Small reversing black and white checkerboards were presented to the participants sequentially at three different frequencies (8 Hz, 14 Hz, and 28 Hz) during the recordings. The brain signal acquisition was performed at a sampling rate of 256 Hz with 128 active electrodes using the ABC layout standard for electrode placement. The EEG recordings were re-referenced using the central Cz electrode and band-pass filtered from 6 Hz to 35 Hz. The subjects experienced a visual stimulus for 15 seconds in each trial. Each unique visual stimulus was repeated five times, corresponding to 60 trials (4 subjects×3 stimuli×5 repetitions) in total. Dataset-B, which was provided by another research institute, consisted of EEG recordings of four healthy subjects as well. A flickering box that changes color rapidly from black to white at seven different frequencies (6 Hz, 6.5 Hz, 7 Hz, 7.5 Hz, 8.2 Hz, 9.3 Hz, and 10 Hz) was used as the visual stimulus. The brain signal acquisition was performed at a sampling rate of 512 Hz with three electrodes (Oz, Fpz, Pz) using the 10-20 layout standard for electrode placement. The EEG recordings were referenced using the electrode Fz, and an analog notch filter at 50 Hz was applied to suppress the power-line noise. The subjects experienced a visual stimulus for 30 seconds in each trial. Each unique visual stimulus was repeated at least three times, with 92 trials in total. An overview of these datasets is provided in Table I.

The most common measurement to evaluate the performance of a BCI system is the information transfer rate (ITR) which can be expressed in bits/minutes as follows:

$$ITR = s\left[\log_2(N) + p\log_2 p + (1-p)\log_2\left(\frac{1-p}{N-1}\right)\right]$$

where N stands for the number of equiprobable commands, s denotes the commands performed per minute, and p represents the accuracy of target detection. In general, the BCIs that exhibit a high ITR have a large number of commands. However, N is fixed in the exemplary datasets, and the joint optimization of s and p boost the ITR. Also, a

TABLE I

SSVEP DATASETS

| Dataset | # of Subjects | # of Trials | Record Length | Sampling Rate | # of Channels | # of Stimulus Frequencies | Stimulus Frequencies |
|---------|---------------|-------------|---------------|---------------|---------------|---------------------------|----------------------|
| A | 4 | 60 | 15 s | 256 | 128 | 3 | 8 Hz, 14 Hz, 28 Hz |
| B | 4 | 92 | 30 s | 512 | 3 | 7 | 6 Hz, 6.5 Hz, 7 Hz, 7.5 Hz, 8.2 Hz, 9.3 Hz, 10 Hz | threshold can be set either on s or p based on the user comfort. For example, a user may not prefer an average detection accuracy of 60%, even though the ITR is high with a short detection duration.

In various embodiments of the present invention, the pre-processed EEG signal from the occipital channel (Oz) is segmented with an overlap, and each segment is windowed using a Hamming function. Afterwards, the power spectral density of the signal is estimated as follows:

$$S_{EEG}[f] = \frac{1}{N}\left|\sum_{n=0}^{N-1} EEG[n] \cdot w[n] \cdot e^{-j\left(\frac{2\pi fn}{N}\right)}\right|^2$$

where EEG[n] and w[n] represents the discrete EEG signal and Hamming window function, respectively. The features for SSVEP detection are extracted by multiplying the $S_{EEG}[f]$ with the filter banks. The filter banks are optimized to deal with the inherent characteristics of the SSVEPs. The SSVEP response power to a flickering visual stimulus is frequency selective and it gets weaker as the frequency of the stimuli increases. Although the EEG background noise power decreases as well (approximately with a 1/f behavior), the resultant SNR is still considerably low at high frequencies. Hence, the gain and bandwidth of the filters are tuned based on these SSVEP characteristics.

Assuming that there are K target stimulus frequencies $f_1, f_2, \ldots, f_K$ in a BCI system, the array of filters are expressed by the following equation:

$$H_k[f]: \begin{cases} \frac{f-(f_k - BW_k/2)}{BW_k} * g_k, & (f_k - BW_k/2) \leq f \leq f_k \\ \frac{(f_k + BW_k/2) - f}{BW_k} * g_k, & f_k \leq f \leq (f_k + BW_k/2) \\ 0, & \text{otherwise} \end{cases}$$

where $BW_k$ and $g_k$ represent the bandwidth and gain of the $k^{th}$ filter, respectively. Initially, higher bandwidth and gain are set to frequencies with low SSVEP response. Subsequently, these parameters are optimized for individual users in order to counter frequency selective nature of SSVEP response. Furthermore, the optimized gains are changed over time to incorporate the time variation of the SSVEP response. A grid search algorithm performs this hyper-parameter optimization through a manually specified subset of the hyper-parameter space. The shape of the triangular waveform in the filter banks is chosen to emphasize the center frequency without completely omitting the adjacent frequencies. The spontaneous EEG activities typically do not present any harmonic components, and hence the SSVEP harmonics are included in the filterbanks (i.e., $H_{k+1}[f]$ for $2*f_1, \ldots, H_{k+k}[f]$ for $2*f_K$) to improve the detection accuracy. Therefore, the elements of feature vector (X) are calculated as follows:

$$x_i = \sum_f S_{EEG}[f] * H_i[f]$$

$$i = 1, \ldots, 2K$$

The extracted features are classified with a logistic regression model using a one-vs-all strategy. Assuming K classes where each class represents a target stimulus frequency. The hypothesis function ($h_\theta(X)$) predicts the binary output variable (y) which shows whether the given input belongs to a class or not, and it is defined for each class as follows:

$$h_\theta^{(k)}(X) = g(\theta^T X) = \frac{1}{1+e^{-\theta^T X}}$$

$$k = 1, \ldots, K$$

where g represents the sigmoid function, X denotes the feature vector with a size of 2K+1 where $x_0=1$, $\theta$ stands for the mapping weight vector which has same size with X, and k is the indicator for the classes. $\theta$ is chosen in such away that it minimizes the cost function $J(\theta)$ which is a distance metric between the prediction and the actual output as follows:

$$J(\theta) = \frac{1}{M}\sum_{m=1}^{M}[-y^{(m)}\log(h_\theta(x^{(m)})) - (1-y^{(m)})\log(1-h_\theta(x^{(m)}))] + \frac{\lambda}{2M}\sum_{j=1}^{2K+1}\theta_j^2$$

where $\{(x^{(m)}, y^{(m)}; m=1, \ldots, M\}$ represents the training set and $y \in \{0,1\}$. The last additional term prevents overfitting the classifier and its precision is controlled by the regularization parameter $\lambda$. $J(\theta)$ is minimized with a gradient descent algorithm and optimizal $\theta$ is found for each class.

The training dataset is split using a leave-one-out methodology. More specifically, each trial is tested using the data from other trials within a subject. After the training stage, the probability of each class is calculated using the hypothesis function and the class with the highest probability labeled as a candidate target frequency detection as follows:

$$f_k = \mathrm{argmax}_k h_\theta^{(k)}(X)$$

The SSVEP frequency is labeled as detected when the same frequency ($f_k$) occurs at least three times in the last four iterations. If the selection criteria is not satisfied during the given time period, it is evaluated as an unsuccessful detection.

To evaluate the improvement provided by the present invention, the proposed algorithm was compared with the performance of two well-known SSVEP frequency detection methods, namely power spectral density analysis (PSDA) and canonical correlation analysis (CCA). Additionally, the bio-inspired filter banks of the present invention were replaced with unit filters, to observe the effect of the proposed design.

A unit filter (UF) algorithm, following the same procedure except for the utilization of the bio-inspired filter banks was investigated. Instead of the bio-inspired filter banks (BIM), the unit filters (UF) were used in the SSVEP recognition algorithm, and they are expressed as follows:

$$HU_k(f): \begin{cases} 1, & (f_k - 0.5) \le f \le (f_k + 0.5) \\ 0, & \text{otherwise} \end{cases}$$

As such, any performance difference, when compared to the proposed approach of the present invention, can be attributed to the bio-insired filter bank design of the present invention.

In accordance with the power spectral density analysis (PSDA) technique, the pre-processed EEG signal from the occipital channel (Oz) is segmented, and each segment is windowed using a Hamming function, similar to the proposed approach of the present invention. The class values which correspond to each target frequency are calculated, and the maximum class is detected as the SSVEP target frequency as follows:

$$c_i = \sum_f S_{EEG}[f] * HU_i[f] + \sum_f S_{EEG}[f] * HU_i[2f]$$

$$i = 1, \ldots, 2K$$

$$f_k = \max_k c_k$$

The canonical correlation analysis (CCA) is a multivariable statistical method which is known for SSVEP frequency detection. In summary, if X is a multichannel EEG signal, Y is the "Fourier series" of a simulated stimulus signal, and w is a linear combination coefficient. CCA searches for the linear combination that maximizes the correlation between $U=w_x^T X$ and $V=w_y^T Y$ by optimizing the following equation:

$$\max_{w_x, w_y} \rho = \frac{E[w_x^T XY^T w_y]}{\sqrt{E[w_x^T XX^T w_x]E[w_y^T YY^T w_y]}}$$

Only the highest correlation of canonical variables U and V are used for the frequency detection and this step is repeated for each simulated stimulus signal's Fourier series, Y. The stimuli frequency which provides the highest correlation among other stimuli frequencies is detected as the actual SSVEP frequency. Similar to PSDA and BLEB, the same EEG preprocessing steps are applied for the CCA method, as well To compare the various methods; the bio-inspired filter bank method of the present invention for SSVEP frequency detection was tested on eight subjects comprising 152 trials, in total, using two datasets. The results which compare the method of the present invention with the three baseline methods, UF, PSDA and CCA, are listed in Table II & Table III. It should be pointed out that ITR changes logarithmically with the number of available commands and since the number of commands between two datasets are different, ITRs need to be compared separately for each dataset.

TABLE II

PERFORMANCE COMPARISON ON DATASET-A

Dataset - A
No of Commands = 3 [8 Hz, 14 Hz, 28 Hz], MDT = Mean Detection Time

| | | PSDA | | | CCA | | | UF | | | BIFB | | |
|---|---|---|---|---|---|---|---|---|---|---|---|---|---|
| Subject | # of Trials | MDT (sec) | Acc. (%) | ITR (bits/min) | MDT (sec) | Acc. (%) | ITR (bits/min) | MDT (sec) | Acc. (%) | ITR (bits/min) | MDT (sec) | Acc. (%) | ITR (bits/min) |
| I | 15 | 5.00 | 66.67 | 4.00 | 3.50 | 73.33 | 8.26 | 5.85 | 86.67 | 9.08 | 5.40 | 100 | 17.61 |
| II | 15 | 7.00 | 73.33 | 4.13 | 2.50 | 66.67 | 8.00 | 4.50 | 80.00 | 8.84 | 5.55 | 100 | 17.13 |
| III | 15 | 5.00 | 73.33 | 5.78 | 4.25 | 66.67 | 4.71 | 4.70 | 100 | 20.23 | 4.27 | 100 | 22.29 |
| IV | 15 | 9.00 | 53.33 | 0.81 | 3.00 | 66.67 | 6.67 | 7.75 | 66.67 | 2.58 | 6.05 | 93.33 | 11.55 |

TABLE III

PERFORMANCE COMPARISON ON DATASET-B

Dataset - B
No of Commands = 7 [6 Hz, 6.5 Hz, 7 Hz, 7.5 Hz, 8.2 Hz, 9.3 Hz, 10 Hz], MDT = Mean Detection Time

| | | PSDA | | | CCA | | | UF | | | BIFB | | |
|---|---|---|---|---|---|---|---|---|---|---|---|---|---|
| Subject | # of Trials | MDT (sec) | Acc. (%) | ITR (bits/min) | MDT (sec) | Acc. (%) | ITR (bits/min) | MDT (sec) | Acc. (%) | ITR (bits/min) | MDT (sec) | Acc. (%) | ITR (bits/min) |
| I | 24 | 7.25 | 87.50 | 16.06 | 5.25 | 87.50 | 22.18 | 4.55 | 88.42 | 26.23 | 4.47 | 88.38 | 26.67 |
| II | 26 | 3.75 | 80.77 | 25.66 | 3.50 | 80.77 | 27.50 | 3.43 | 88.73 | 35.15 | 3.03 | 88.31 | 39.36 |
| III | 21 | 3.75 | 80.95 | 25.80 | 3.50 | 85.71 | 31.65 | 3.80 | 80.95 | 25.48 | 5.19 | 100 | 32.45 |
| IV | 21 | 8.00 | 85.71 | 13.85 | 7.00 | 100 | 24.06 | 3.94 | 95.24 | 36.67 | 4.13 | 100 | 40.78 |

The traditional PSDA method requires longer time windows; compared to the other two methods, to improve the accuracy, thereby resulting in a lower ITR. CCA, on the other hand, is successful on shorter time windows, providing high ITR but lower accuracy. The accuracy can subsequently be improved by using longer time windows with lower ITR trade-off. Moreover, the performance of CCA in Dataset-A is poor since it is insufficient and incompatible to detect 2.8 Hz.

Both tables show that the BIFB method of the present invention provides reliable accuracy and sufficient ITR performance. As such, the proposed approach is significantly better to detect the SSVEP responses at high frequencies, when compared to other techniques known in the art.

Figure 5:
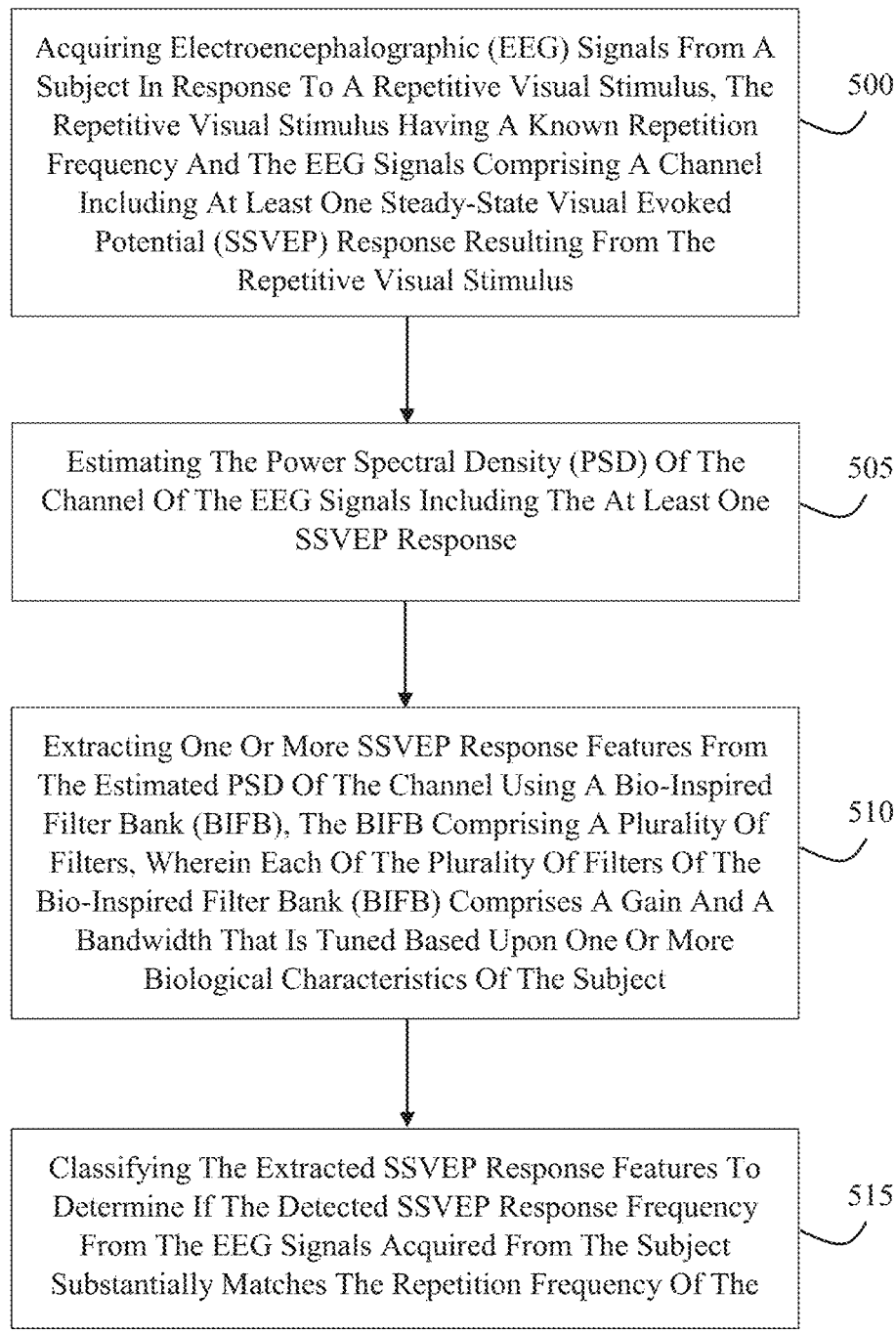
FIG. 5 is a flowchart illustrating the method of the present invention for detecting the response of a user from an SSVEP signal, in accordance with an embodiment of the present invention.

With reference to FIG. 5, a method for steady-state visual evoked potential (SSVEP) frequency detection using a bio-inspired filter bank (BIFB) is illustrated.

In a first step of the method, a communication channel between a subject and an EEG device may be used for acquiring electroencephalographic (EEG) signals from a subject in response to a repetitive visual stimulus, the repetitive visual stimulus having a known repetition frequency and the EEG signals comprising a channel including at least one steady-state visual evoked potential (SSVEP) response resulting from the repetitive visual stimulus 505.

At a second step of the method, a processor of brain-computer interface (BCI) may be configured for estimating the power spectral density (PSD) of the channel of the EEG signals including e at least one SSVEP response 510.

At a third step, the processor of the BCI may further be configured for extracting one or more SSVEP response features from the estimated PSD of the channel using a bio-inspired filter bank (BIFB), the BIFB comprising a plurality of filters, wherein each of the plurality of filters of the bio-inspired filter bank (BIFB) comprises a gain and a bandwidth that is tuned based upon one or more biological characteristics of the subject 515 and for classifying the extracted SSVEP response features to determine if the SSVEP response frequency from the EEG signals acquired from the subject substantially matches the repetition frequency of the repetitive visual stimulus 520.

Accordingly, in various embodiments, the present invention provides a novel SSVEP detection method inspired by the biological characteristics of the SSVEP. The inventive method not only improves the accuracy of the detection but also increases the available number of commands by allowing the use of stimuli frequencies that elicit weak SSVEP responses. The bio-inspired filter bank (BIFB) method of the present invention achieves reliable performance metrics when tested on datasets available online and compared with well-known SSVEP frequency detection methods as baseline methods: PSDA and CCA.

The present invention may be embodied on various computing platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any, appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a
particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method for steady-state visual evoked potential (SSVEP) frequency detection using a bio-inspired filter bank (BIFB), the method comprising:
acquiring electroencephalographic (EEG) signals from a subject in response to a repetitive visual stimulus of a target that the subject is attentive to the repetitive visual stimulus having a known repetition frequency and the EEG signals comprising a channel including at least one SSVEP response resulting from the repetitive visual stimulus;
estimating the power spectral density (PSD) of the channel of the EEG signals including the at least one SSVEP response;
extracting one or more SSVEP response features from the estimated PSD of the channel using the BIFB, the BIFB comprising a plurality of filters, wherein each of the plurality of filters of the BIFB comprises a gain and a bandwidth that is tuned based upon one or more biological characteristics of the subject and wherein the gain and bandwidth of each of the plurality of filters of the BIFB are adjusted over time to account for a time variance of the at least one SSVEP response; and classifying the extracted SSVEP response features to determine if the detected SSVEP response frequency from the EEG signals acquired from the subject substantially matches the repetition frequency of the repetitive visual stimulus of the target.

2. The method of claim 1, wherein the one or more biological characteristics of the subject include a subject-specific frequency sensitivity.

3. The method of claim 1, wherein BIFB includes an array of band-pass filters having a center frequency at the known repetition frequency of the repetitive visual stimulus and the associated harmonics.

4. The method of claim 1 further comprising, pre-processing the acquired EEG signals to remove one or more unwanted components from the EEG signals and to increase the signal-to-noise ratio (SNR) of the EEG signals, prior to extracting one or more SSVEP features.

5. The method of claim 1, wherein the channel is an occipital channel (Oz) of the acquired EEG signals.

6. The method of claim 2 further comprising, segmenting the pre-processed EEG signal from the channel prior to estimating the power spectral density (PSD) of the channel.

7. The method of claim 1, wherein extracting one or more SSVEP features from the estimated PSD of the channel using the BIFB further comprises, multiplying the estimated PSD by one or more of the plurality of filters of the BIFB.

8. A system for steady-state visual evoked potential (SSVEP) frequency detection using a bio-inspired filter bank (BIFB), the system comprising:
   a brain-computer interface comprising input circuitry for receiving EEG signals from a subject in response to a repetitive visual stimulus generated by a target that the subject is attentive to, the EEG signals comprising a channel including the at least one detected SSVEP response frequency resulting from the repetitive visual stimulus; and
   the brain-computer further comprising one or more processors for estimating the power spectral density (PSD) of the channel of the EEG signals including the at least one SSVEP response, for extracting one or more SSVEP response features from the estimated PSD of the channel using the BIFB, the BIFB comprising a plurality of filters, wherein each of the plurality of filters of the BIFB comprises a gain and a bandwidth that is tuned based upon one or more biological characteristics of the subject, and wherein the gain and bandwidth of each of the plurality of filters of the BIFB are adjusted over time to account for a time variance of the at least one SSVEP response, and for classifying the extracted SSVEP response features to determine if the detected SSVEP response frequency from the EEG signals acquired from the subject substantially matches the repetition frequency of the repetitive visual stimulus of the target.

9. The system of claim 8, wherein the one or more biological characteristics of the subject include a subject-specific frequency sensitivity.

10. The system of claim 8, wherein BIFB includes an array of band-pass filters having a center frequency at the known repetition frequency of the repetitive visual stimulus and the associated harmonics.

11. The system of claim 8 further comprising, pre-processing the acquired EEG signals to remove one or more unwanted components from the EEG signals and to increase the signal-to-noise ratio (SNR) of the EEG signals, prior to extracting one or more SSVEP features.

12. The system of claim 8, wherein the channel is an occipital channel (Oz) of the acquired EEG signals.

13. The system of claim 8 further comprising, segmenting the pre-processed EEG signal from the channel prior to estimating the power spectral density (PSD) of the channel.

14. The system of claim 8, wherein extracting one or more SSVEP features from the estimated PSD of the channel using the BIFB further comprises, multiplying the estimated PSD by one or more of the plurality of filters of the BIFB.

15. One or more non-transitory computer-readable media having computer-executable instructions for performing a method of running a software program on a computing device, the computing device operating under an operating system, the method including issuing instructions from the software program comprising:
   acquiring electroencephalographic (EEG) signals from a subject in response to a repetitive visual stimulus of a target that the subject is attentive to, the repetitive visual stimulus having a known repetition frequency and the EEG signals comprising a channel including at least one steady-state visual evoked potential (SSVEP) response resulting from the repetitive visual stimulus;
   estimating the power spectral density (PSD) of the channel of the EEG signals including the at least one SSVEP response;
   extracting one or more SSVEP response features from the estimated PSD of the channel using a bio-inspired filter bank (BIFB), the BIFB comprising a plurality of filters, wherein each of the plurality of filters of the BIFB comprises a gain and a bandwidth that is tuned based upon one or more biological characteristics of the subject and wherein the gain and bandwidth of each of the plurality of filters of the BIFB are adjusted over time to account for a time variance of the at least one SSVEP response; and
   classifying the extracted SSVEP response features to determine if the detected SSVEP response frequency from the EEG signals acquired from the subject substantially matches the repetition frequency of the repetitive visual stimulus of the target.

16. The media of claim 15, wherein the one or more biological characteristics of the subject include a subject-specific frequency sensitivity.

17. The media of claim 15, wherein the method including issuing instructions from the software program further comprises, issuing instructions for the BIFB which includes an array of band-pass filters having a center frequency at the known repetition frequency of the repetitive visual stimulus and the associated harmonics.

* * * * *